United States Patent [19]

Rucker et al.

[11] Patent Number: 4,990,312

[45] Date of Patent: Feb. 5, 1991

[54] HIGH-PRESSURE PROMOTED COMBUSTION CHAMBER

[75] Inventors: Michelle A. Rucker; Joel M. Stoltzfus, both of Las Cruces, N. Mex.

[73] Assignee: The United States of America as represented by the Administrator of the National Aeronautics and Space Administration, Washington, D.C.

[21] Appl. No.: 381,239

[22] Filed: Jul. 18, 1989

[51] Int. Cl.[5] ............................................. G01N 31/12
[52] U.S. Cl. ...................................... 422/78; 422/80; 422/104; 374/8; 73/865.6
[58] Field of Search ................... 422/78, 79, 80, 104; 374/8; 73/865.6

[56] References Cited

U.S. PATENT DOCUMENTS

| | | | |
|---|---|---|---|
| 2,659,235 | 11/1953 | Storer | 73/432 |
| 2,917,927 | 12/1959 | Clark | 73/432 |
| 2,937,530 | 5/1960 | Haley | 73/432 |
| 3,107,981 | 10/1963 | Honma et al. | 422/78 |
| 3,186,801 | 6/1965 | Hampton | 23/253 |
| 3,188,180 | 6/1965 | Holler | 23/230 |
| 3,421,856 | 1/1969 | Stenger et al. | 23/230 |
| 3,545,252 | 12/1970 | Springfield et al. | 73/15 |
| 3,578,756 | 5/1971 | Evans et al. | 73/15 |
| 3,926,562 | 12/1975 | Williams et al. | 422/78 X |
| 3,987,661 | 10/1976 | Kamp et al. | 374/8 |
| 4,637,735 | 1/1987 | de Ris et al. | 422/80 X |

*Primary Examiner*—Robert J. Warden
*Assistant Examiner*—Jeffrey R. Snay
*Attorney, Agent, or Firm*—Russell E. Schlorff; John R. Manning; Edward K. Fein

[57] ABSTRACT

In the preferred embodiment of the promoted combustion chamber disclosed herein, a thick-walled tubular body that is capable of withstanding extreme pressures is arranged with removable upper and lower end closures to provide access to the chamber defined within the body. A bracket is arranged in the chamber for dependently supporting a test sample of a material being evaluated in the chamber. To facilitate the real-time analysis of a test sample, several pressure-tight viewing ports capable of withstanding the simulated environmental conditions are arranged in the walls of the tubular body for observing the test sample during the course of a test. A replaceable heat-resistant tubular member and replaceable flame-resistant internal liners are arranged to be fitted inside of the chamber for protecting the interior wall surfaces of the combustion chamber during the evaluation tests. Inlet and outlet ports are provided for admitting high-pressure gases into the chamber as needed for carrying out dynamic analyses of the test sample during the course of an evaluation test.

32 Claims, 3 Drawing Sheets

HIGH-PRESSURE PROMOTED COMBUSTION CHAMBER

ORIGIN OF THE INVENTION

The invention described herein was made by employees of the United States Government and may be manufactured and used by or for the Government of the United States of America for governmental purposes without the payment of any royalties thereon or therefor.

BACKGROUND OF THE INVENTION

1. Field of the Invention

High-pressure oxygen is commonly used in various medical devices and diving equipment as well as a typical oxidizer for liquid bipropellant propulsion systems in manned and unmanned spacecraft.

This invention relates to testing apparatus for evaluating the suitability of materials that are proposed to be used in equipment which will utilize high-pressure gases or will be exposed to high-pressure gaseous environments. More particularly, the present invention is related to a new and improved high-pressure promoted combustion chamber for conducting multiple real-time analyses of metallic and nonmetallic test samples subjected to inert or oxidizing gases under selectively-controlled environmental conditions.

2. Background Art

Heretofore environmental test chambers such as shown in U.S. Pat. Nos. 2,659,235, 2,917,927 and 2,937,530 have been employed for determining if various electrical or mechanical devices can be safely operated in a potentially-explosive gaseous atmosphere without generating excessive heat or creating sparks that might possibly ignite the gaseous mixture. Typically these test chambers include an explosion-resistant enclosure sized to contain the device that is to be tested and a blower for circulating the potentially-explosive gas through the test chamber. The test is then conducted by operating the device inside of the enclosure to determine if an explosion occurs when the device is operated in that particular environment.

To test combustible materials such as synthetic fabrics, a so-called "autoignition" test chamber such as shown in U.S. Pat. No. 3,578,756 is arranged to allow a selected gas to be maintained at a moderate constant pressure inside of the chamber while minute gas samples are periodically withdrawn to determine whether the test specimen is being decomposed. The internal temperature of the chamber is controlled by immersing the chamber in a liquid bath whose temperature is periodically varied during the course of the test. In this way, a series of measurements representative of the decomposition of the tested material are obtained for given temperature ranges and gaseous environments.

In addition to determining whether particular devices can be safely used in potentially-explosive environments, it is particularly useful to establish the flammability or so-called "flame propagation" of various materials that will be subjected to these hazardous environments. A test device which has been found to be well suited for determining the flammability of various plastics and other non-metallic combustible materials in hazardous environments is disclosed in U.S. Pat. No. 3,545,252. As fully described there, a material specimen that is to be tested is put in an enclosed chamber and a source of low-pressure gas is connected to the test chamber. An electric heating coil inside of the test chamber is then selectively positioned in relation to the specimen to control the amount of heat that is being applied to the specimen. A plexiglass window is arranged in one end of the chamber so that laboratory personnel can observe the test specimen as well as accurately position the coil.

Many of the technological advances in aerospace and in medicine in recent years make it essential to evaluate the suitability of materials which are being considered for potential service in gaseous environments. One of the most critical tests of this nature is to determine whether non-combustible materials can be safely used in high-pressure oxygen-enriched environments. Heretofore these evaluation tests have been conducted by enclosing a representative sample of a proposed material in a test chamber and simply subjecting the test sample to a controlled environment for a given length of time to determine whether that material can withstand a particular environmental condition. Although these tests are useful, such static tests are nevertheless limited since only post-test analyses can be made of the remains of the test sample. It is, of course, appreciated by those skilled in the art that with the typical static test chambers of the prior art, investigators are unable to make real-time studies of the flame propagation of materials under predetermined dynamic test conditions in high-pressure inert or oxidizing gaseous environments.

STATEMENT OF THE INVENTION

Accordingly, it is an object of the present invention to provide new and improved high-pressure combustion chambers for making real-time dynamic analyses of materials proposed for use in high-pressure gaseous environments.

It is a further object of the invention to provide new and improved promoted-combustion test chambers which are arranged for successively conducting a number of dynamic real-time analyses of selected non-metallic and metallic materials under simulated environmental conditions that are representative of the operating conditions that components formed of these materials may be subsequently exposed to in a particular service involving high-pressure gases.

It is still another object of the present invention to provide new and improved promoted-combustion chambers which can be readily opened and easily reconditioned by replacing any internal elements that were damaged in a previous test.

It is an additional object of the present invention to provide new and improved promoted-combustion chambers with replaceable internal elements that are completely accessible by way of closure members that can be readily removed so the combustion chambers can be easily reconditioned by quickly replacing any of these internal elements that were damaged in a previous test and installing a new test specimen.

It is another object of the present invention to provide new and improved promoted-combustion test chambers arranged to be quickly opened and closed to facilitate dynamic and static testing of a large number of material samples under simulated hazardous environment conditions.

These and other objects of the invention are attained by providing a hollow body with an internal chamber arranged for supporting a test sample of a material being evaluated for use in apparatus or components proposed for service in hazardous high-pressure gaseous environments. To facilitate the real-time analysis of the test sample, pressure-tight viewing ports that are capable of withstanding the simulated environmental conditions are provided for observing the test sample during a test. Replaceable flame-resistant liners are arranged to protect the interior wall surfaces of the chamber so that the hollow body itself will not burn during evaluation tests. Inlet and outlet ports are also arranged for passing high-pressure gases into the chamber as may be required to carry out various dynamic analyses of the test sample during an evaluation test.

BRIEF DESCRIPTION OF THE DRAWINGS

The several features of the invention are set forth with particularity in the appended claims. The arrangement and practice of the invention, together with further objects and various advantages thereof, may best be understood by way of the following description of an exemplary apparatus which incorporates the principles of the invention as illustrated in the accompanying drawings, in which:

DETAILED DESCRIPTION OF THE PREFERRED EMBODIMENT

Figure 1:
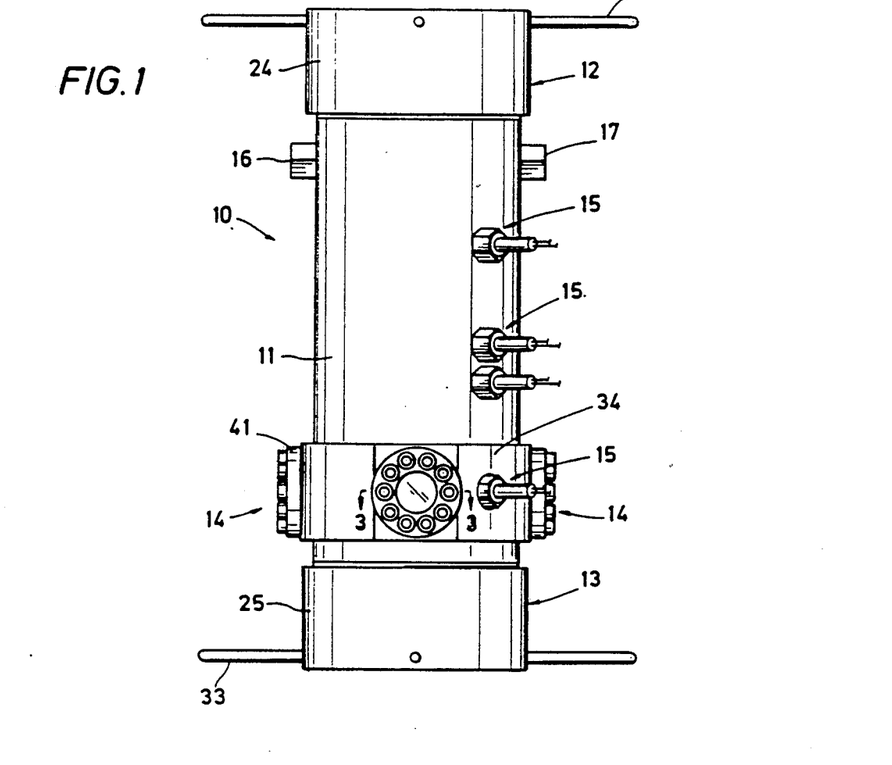
FIG. 1 is an elevational view of a preferred embodiment of a high-pressure combustion chamber arranged in accordance with the principles of the present invention.

Turning now to FIG. 1 an external elevational view is shown of a preferred embodiment of a high-pressure chamber 10 arranged in accordance with the principles of the present invention. As depicted, the combustion chamber 10 includes a thick-walled tubular body 11 which is capped at each end with easily-removable upper and lower end closures as shown generally at 12 and 13. To facilitate carrying out real-time analyses of a test sample (not depicted in FIG. 1) that is mounted in the combustion chamber 10, pressure-tight viewing ports, as indicated generally at 14 and 15, having windows capable of withstanding the anticipated simulated environmental conditions within the combustion chamber are arranged at selected locations on the tubular body 11 for observing the enclosed sample during the course of a test. Threaded inlet and outlet gas ports 16 and 17 are arranged on opposite sides of the body 11 to facilitate the admission of high-pressure gases into or through the chamber 10 as may be required for carrying out various dynamic analyses of the enclosed test sample in the combustion chamber.

Figure 2:
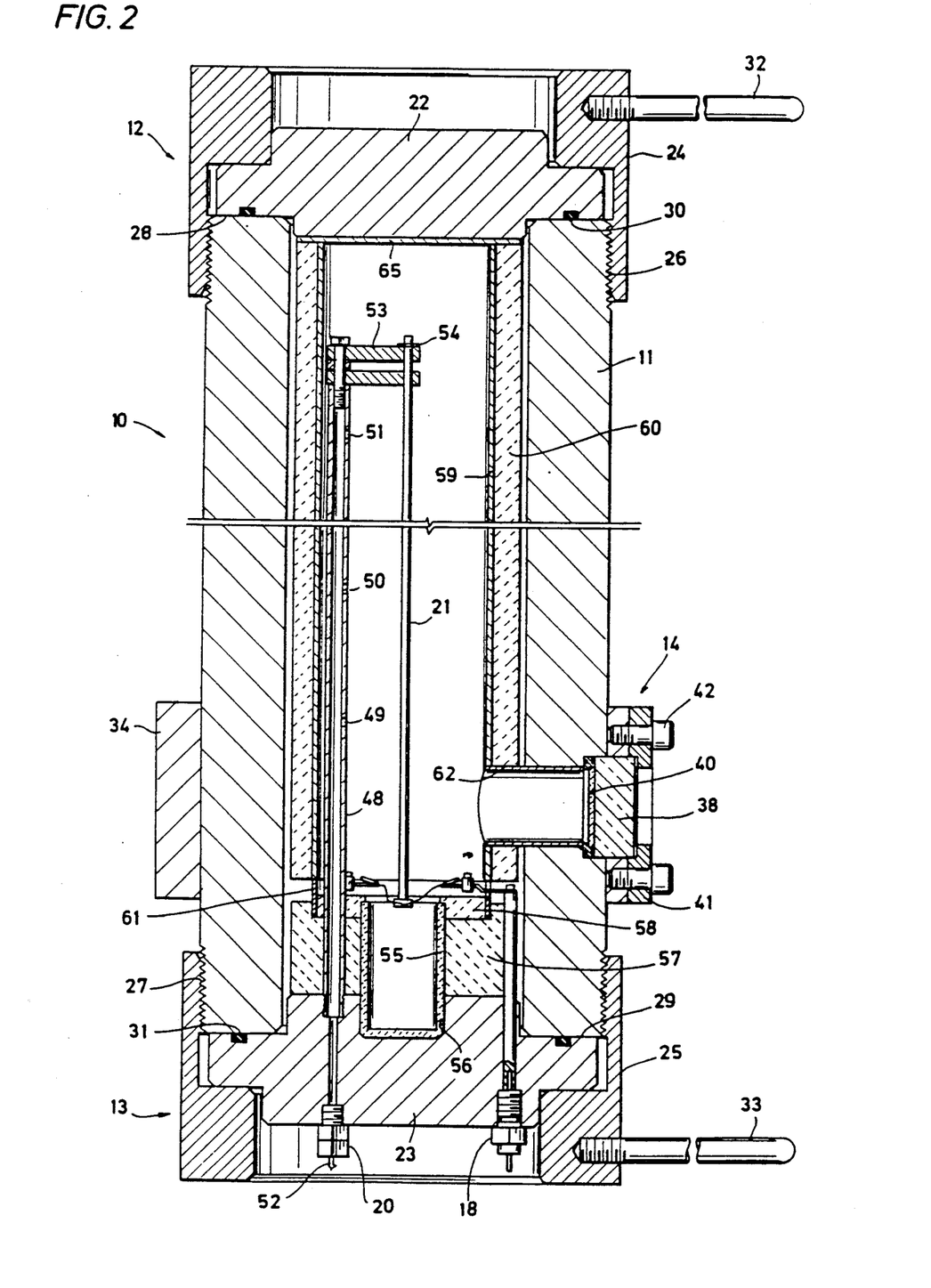
FIG. 2 is an enlarged cross-sectioned elevational view of the upper and lower portions of the combustion chamber shown in FIG. 1.

Turning now to FIG. 2, a cross-sectioned elevational view is shown of the upper and lower portions of the chamber 10. High-pressure electrical feedthrough connectors 18 (and as shown at 19 in FIG. 4) are arranged on the lower end closure 13 for connecting electrical test apparatus in the combustion chamber 10 to an external power source (not shown in the drawings). A high-pressure feedthrough assembly 20 is also arranged on the lower end closure 13 to fluidly seal around the leads from various thermocouple junctions mounted in the chamber 10 which pass through the feedthrough and are connected to associated measuring apparatus (not shown in the drawings) outside of the combustion chamber. As will be subsequently explained in more detail, a typical test sample 21 is positioned within the thick-walled body 11 as may be required for testing a particular material or device.

The upper and lower end closures 12 and 13 include thick circular plates 22 and 23 respectively placed across the transverse upper and lower end surfaces of the thick-walled tubular body 11. The thick-walled body 11 and these end cover plates 22 and 23 are preferably formed from high-strength corrosion-resistant stainless steels which have physical properties and thicknesses commensurate with the proposed environmental conditions which the combustion chamber 10 will be subjected to.

To releasably secure the end plates 22 and 23 to the body 11, threaded rings 24 and 25 are respectively coupled to the body by complemental threads 26 and 27 and provided with inwardly-projecting shoulders 28 and 29 for clamping the upper and lower end plates between these shoulders and the opposed ends of the thick-walled body as the upper and lower threaded rings are being tightened. Two-piece high-pressure sealing members 30 and 31 are cooperatively arranged near the perimeters of the end plates 22 and 23 to be compressed into sealing engagement against the opposed ends of the body 11 when the upper and lower rings 24 and 25 are tightened on the threads 26 and 27. In the depicted preferred embodiment of the combustion chamber 10, the sealing members 30 and 31 are respectively arranged as an annular member carrying a suitable elastomer sealing ring, with this annular member being formed of a suitable plastic such as poly-ether-ether-ketone having a square or rectangular cross-section sized to close the gap between the end plate, as at 22, and the end of the body 11 as the threaded ring, as at 25, is coupled to the lower end of the thick-walled body 11. To facilitate the rapid installation and the removal of the end closures 12 and 13 without tools, outwardly-projecting bars, as at 32 and 33, are respectively spaced around the threaded rings 24 and 25 and arranged for providing diametrically-opposed handles of sufficient length and mechanical strength to enable the upper and lower rings to be manually tightened and loosened on the threads 26 and 27 without undue effort.

The larger viewing ports 14 are uniformly disposed around the lower portion of the thick-walled body 11 and preferably arranged to provide at least two diametrically-opposed ports on opposite sides of the body to facilitate using either an X-ray or infrared camera to observe the test sample 21 when the combustion chamber 10 is filled with smoke, flame or a particulate which would otherwise obscure the view. In the preferred manner of arranging the combustion chamber 10, there are four of these larger viewing ports 14 to allow simultaneous X-ray, video and pyrometer monitoring during a test operation. To enable the viewing ports 14 to be larger than would otherwise be possible for a given thick-walled body, the larger ports are located in an outwardly-enlarged reinforcing section 34 in the lower portion of the thick-walled body 11. It will, of course, be recognized that the reinforcing section 34 may alternatively be arranged either as an integral portion of the thick-walled tubular body or, as illustrated in the drawings, as a separate member that is press-fitted onto the body 11.

Figure 3:
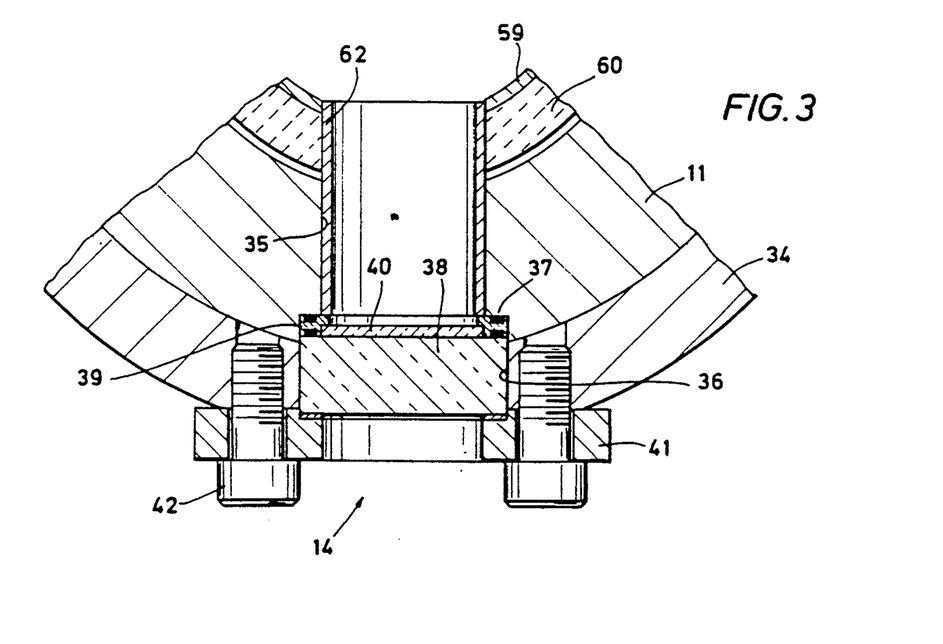
FIG. 3 is an enlarged partial cross-sectioned plan view of the combustion chamber along the lines "3—3" of FIG. 1.

As best seen in FIG. 3, in the preferred arrangement of the larger viewing ports 14, lateral bores, as at 35, are respectively provided in the thick-walled body 11 and each counterbored, as at 36, for defining an outwardly-facing shoulder, as at 37, around the mid-portion of the lateral bore. A thick cylindrical block, as at 38, of an optical-grade transparent material such as sapphire is disposed in each counterbore 36; and each block is supported around its peripheral margin by a sealing ring, as at 39, having inner and outer sealing members on its opposite faces for fluidly sealing the transparent blocks in relation to the tubular body 11. It will, of course, be recognized that the blocks 38 must be of sufficient thickness to withstand an extreme pressure such as 10,000-psig. To protect the transparent blocks 38 from flames and metal splatters in the combustion chamber 10, thin quartz discs 40 are respectively disposed on the outer face of each sealing ring 39 for covering the inwardly-directed face of its associated transparent block. The transparent blocks 38 are secured in their respective counterbores 36, by a thick annular flange, as at 41, that is placed over each of the transparent blocks and secured to the body 11 by a plurality of threaded bolts or cap screws, such as at 42, uniformly arranged around the annular flanges and secured to the thick-walled reinforcing section 34. The reinforcing section 34 will, of course, significantly serve to strengthen that portion of the thick-walled tubular body 11 where the larger viewing ports 14 are located.

Figure 5:
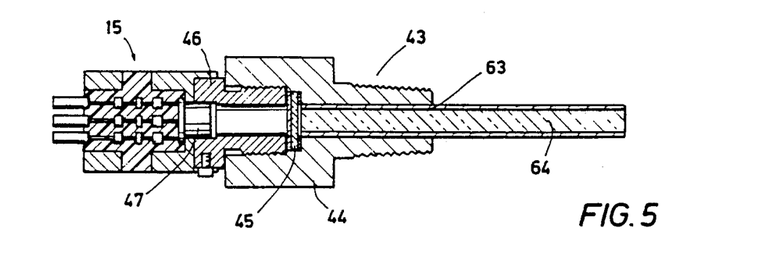
FIG. 5 is an enlarged cross-sectional view of a heat-responsive instrumentation device used in the combustion chamber of the present invention.

As best seen in FIG. 5, in the illustrated preferred embodiment of the combustion chamber 10, each of the smaller viewing ports 15 is a self-contained high-pressure sight glass assembly including an elongated, threaded tubular body 43 having an enlarged counterbored portion 44 carrying an optically-transparent window 45 that is fluidly sealed in the counterbored portion 40 between protective annular washers. The counterbored portion 44 in each of the tubular bodies 43 is internally threaded to receive a tubular adapter 46 that has an enlarged counterbored portion cooperatively arranged to receive the forward end portion of a typical thermopile assembly 47 for detecting radiant heat. It will, of course, be appreciated by those skilled in the art that the specific locations of these smaller viewing ports 15 carrying the several thermopile assemblies 47 will be wholly dependent on the particular nature of the tests planned for the new and improved combustion chamber 10 of the invention.

As best seen in FIG. 2, in the preferred embodiment of the combustion chamber 10, an upright, elongated tubular support 48 is mounted adjacent to one edge of the lower end plate 23 and extended upwardly inside of the body 11 to a convenient elevation above the upper face of the end plate. Longitudinally-spaced ports are appropriately arranged for spatially positioning the measuring junctions, as at 49 and 50, of thermocouples at intermediate locations along the tubular support 48 as required to measure temperatures at those intermediate elevations in the combustion chamber 10. If desired, the upper end portion of the tubular support 48 can also be arranged for positioning a measuring junction, as at 51, as required for measuring temperatures at higher elevations of the combustion chamber 10. It will also be recognized that by enclosing the thermocouple leads, as at 52, within the tubular support 48, these leads will be safely isolated from the adverse conditions that may be present in the combustion chamber 10 during the course of a test. Moreover, by enclosing the leads 52 inside of the tubular support 48, they can be conveniently directed through the pressure-tight feedthrough assembly 20 in the lower end plate 23 for connection to the temperature-measurement instrumentation (not shown in the drawings) outside of the chamber 10.

It will, of course, be recognized that test samples of any convenient size and desired geometrical configuration can be evaluated in the new and improved combustion chamber 10 of the present invention. In keeping with the objects of the invention, it is greatly preferred that the test samples be supported in such a manner that successive samples of the safe arrangement can be accurately and quickly positioned in the same location within the combustion chamber 10 so as to carry out as many evaluations as possible in a given time period. Accordingly, as illustrated in FIG. 2, to test an elongated test sample, such as at 21, one or more laterally outstanding brackets, as at 53, are cooperatively arranged on the upper end of the tubular support 48 for dependently suspending the test sample in coincidental alignment with the central axis of the thick-walled body 11. To facilitate the quick installation of the test sample 21, the sample is inserted through axially-aligned holes in the brackets 53 and dependently supported by a lateral pin 54 placed in a transverse hole located near the upper end of the sample. In this manner, a group of test samples, as at 21, can be successively installed in the combustion chamber 10 and respectively tested with assurance that each of the samples is accurately positioned in the same testing location. It will be understood, of course, that regardless of their size or shapes, the test samples are fabricated from a particular material being investigated. By way of example, with test samples, as at 21, arranged in the form of long rods, it has been found that rods having a diameter of about 1 to 1½ centimeters can be effectively tested in the combustion chamber 10.

It will, of course, be appreciated by those skilled in the art that when a flammability test is being carried out in the combustion chamber 10, there will be a significant temperature increase in the chamber whenever a test sample, as at 21, being investigated begins burning. Moreover, when a metal test sample begins to burn, burning metal will be splattered in every direction and globules of molten metal will begin falling from the metal sample as it is being consumed. Accordingly, to collect molten metal falling from a burning test sample, as at 21, an expendable receptacle or crucible 55 that is formed of a heat-resistant material such as alumina or of a flame-resistant material such as copper is removably positioned in the thick-walled body 11 with the base portion of the crucible being retained in an upwardly-facing recess 56 provided in the lower end plate 23. As depicted, the crucible 55 is also arranged so that its upper rim will be located at about the same elevation as the lower end of the depending test sample 23. A removable annular ceramic or copper insulating shield 57 is coaxially disposed around the upper portion of the crucible 55 and a removable expendable annular cover 58 is mounted on top of the ceramic insulating shield for protecting the lower end plate 23 from splatters of molten metal from a burning test sample as at 21.

Those skilled in the art will, of course, recognize that, in some cases, the combustion chamber 10 may be utilized for evaluating materials under such extreme testing conditions (e.g., gaseous oxygen at pressures in the order of 10,000-psig) that the thick-walled body 11 and the cover plates 22 and 23 would be unable to withstand those environmental conditions and could themselves start burning. Accordingly, to at least minimize damages to the inner wall surfaces of the combustion chamber 10 and reduce thermal stresses in the thick-walled body 11, an expendable thin-walled tubular liner 59 is complementally fitted in an elongated ceramic insulating tube 60. The protective assembly represented by the tubular liner 59 and the insulating tube 60 is removably positioned in the thick-walled body 11 and coaxially mounted on an expendable ring 61 resting on top of the expendable cover 58. Removable expendable tubular liners, as at 62, are positioned in the lateral bores 35 in the thick-walled body 11 and their respective aligned lateral bores provided in the assembled tubular liner 59 and ceramic insulator 60. A replaceable small-diameter tubular liner 63 is similarly mounted in the forward end of each of the tubular bodies 53 carrying the thermopiles 47. A cylindrical body 64 formed a suitable optical material is installed in each of the liners 63 for directing light from a burning test sample to thermopiles 47. It will be recognized that the optical blocks 64 will serve to limit the fields of view of their respective thermopiles as at 47 thus providing more-accurate measurements. A replaceable expendable cover 65 is also placed over the upper end of the protective assembly that is represented by the liner 59 and the ceramic insulator 60 for protecting the lower face of the upper end plate 22 from splatters of molten metal from a burning test sample as at 21. Although various expendable materials can be employed for the liners 59, 62 and 63, the ring 61 and the protective covers 58 and 65 under more-moderate test conditions, for more-extreme test conditions it has been found necessary to use metals such as copper, nickel and typical monel alloys which are heat-resistant and essentially non-flammable in the presence of oxygen at extreme pressures in the order of 10,000-psig. Copper has been found to be an outstanding material for such extreme environmental conditions since it has good thermal shock and flame-resistance properties as well as strength for withstanding these severe conditions during an evaluation test.

Figure 4:
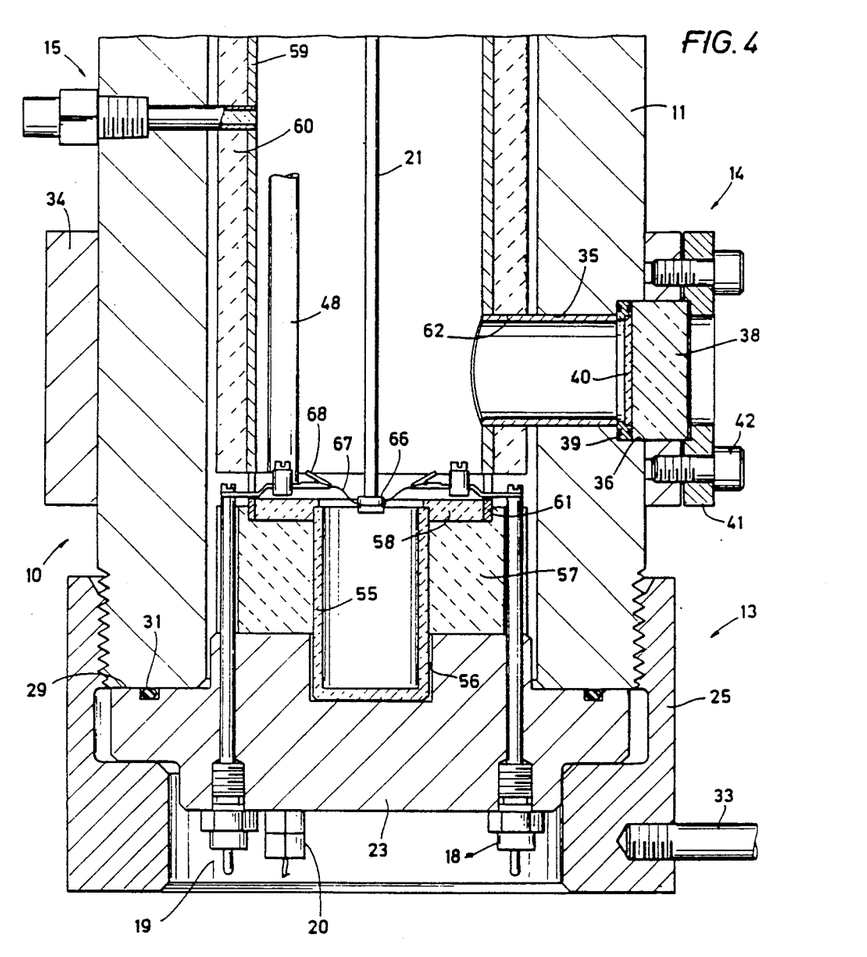
FIG. 4 is an enlarged cross-sectioned elevational view of the lower end portion of the combustion chamber shown in FIG. 1.

In keeping with the objects of the present invention it is preferred to provide means for igniting the test samples, as at 21, which will not unduly hinder the installation of a new test sample into brackets 53 when the combustion chamber 10 is being prepared for a test. Accordingly, an electrical igniter assembly 66 cooperatively arranged to be secured to the lower end of the depending test sample 21 is provided with electrical conductors, as at 67, which are releasably connected to the feedthrough connectors 18 and 19 by means of expendable connectors, such as alligator clips 68, that are respectively mounted on the upper end of a conductive extension, as at 69, of each of the feedthrough connectors 18 and 19. In the preferred arrangement of these igniter assemblies 66, an electrical heating element wire is wrapped around an tubular body of a flammable material, such as magnesium or aluminum, which is press-fitted on the lower end of the elongated rod-like test sample 21, with the end portions of this heating element wire respectively serving as the conductors 67. A typical fuze wire of a resistive alloy of aluminum and palladium has been found to be well adapted for reliably igniting test samples as shown at 21. In those cases where the test sample has a different shape, the igniters for those samples will, of course, have to be appropriately shaped for attachment or mounting on the test sample in such a way as to assure uniform ignition of each test sample in a particular series of tests.

It will be appreciated, therefore, that by preparing a group of these electrical igniters 66 in advance and fitting them on the ends of a group of test samples, as at 21, these prepared samples can be easily and quickly installed in the combustion chamber 10 by simply slipping the upper end of a test sample into the holes in the brackets 53, inserting a pin, as at 54, and connecting the extension conductors 67 to the alligator clips as at 68. Alternatively, should the test procedure call for a large number of tests in a short time, the unique arrangement of the combustion chamber 10 facilitates the advance assembly of individual cover plates 23 and one or more of the various elements shown in FIG. 2 employed for suspending the test sample 21. This has the obvious advantage of allowing a number of these assemblies to be prepared in advance so as to minimize the turn-around time during a prolonged series of tests of various samples as at 21.

Those skilled in the art will, of course, appreciate that as an alternative manner of igniting a test sample, as at 21, an intense energy source, such as a laser beam, can be directed through one of the larger viewing ports 14 so as to be impinged on an adjacent portion of the test sample. If need be, mirrors can, of course, be arranged to direct the laser beam at other portions of a test sample.

Accordingly, it will be appreciated that the combustion chamber of the present invention is particularly adapted to efficiently and rapidly conduct various dynamic and static and dynamic test procedures in a manner which has not been possible heretofore. It will be further recognized that the present invention also provides a new and improved testing chamber for repetitively conducting a series of flammability tests of successive test samples with assurance that each of these test samples will be accurately positioned in the test chamber. By arranging the upper and lower closures 12 and 13 to be easily removed and reinstalled on the thick-walled body 11, the interior of the combustion chamber 10 is always completely accessible to permit a new test sample 21 to be quickly installed. It should also be recognized that the unique arrangement of the combustion chamber 10 facilitates the replacement of all of the protective elements within the thick-walled body 11 as well as the replacement of all of the components of the larger viewing ports 14.

While only a particular embodiment of the apparatus of the present invention has been shown and described herein, it is apparent that various changes and modifications may be made without departing from the principles of the present invention in its broader aspects; and, therefore, the aim in the claims appended hereto is to cover all such changes and modifications as fall within the true spirit and scope of this invention.

What is claimed is:

1. Test apparatus for evaluating samples of materials in a controlled environment comprising:
    a hollow body having interior walls defining an internal chamber and having an access opening in one end thereof for installing a test sample in said chamber;
    inlet and outlet ports in said body for introducing gases into said chamber during an evaluation test;

closure means arranged to be removably installed on said body for sealing said access opening and for gaining access to said chamber:

viewing means for observing a test sample in said chamber including at least one lateral opening in said body, a window disposed in said lateral opening, and means for sealing said window within said lateral opening;

means for protecting the interior walls of said hollow body as a test sample is burning therein including a heat-resistant tubular member having a side opening and removably disposed in said chamber, and a first flame-resistant tubular liner having a side opening and removably disposed in said tubular member and angularly positioned in relation thereto to align said side openings with said lateral opening in said body;

means for protecting said window as a test sample is burning in said chamber including a transparent barrier removably disposed in said lateral opening between said window and said chamber, and a second flame-resistant tubular liner removably disposed in said lateral opening between said transparent barrier and said chamber;

first and second flame-resistant end plates removably disposed at opposite ends of said chamber for protecting the end opposite said one end of said body and said closure means as a test sample is burning in said chamber;

means for supporting a test sample in said chamber inside of said first flame-resistant tubular liner and between said first and second flame-resistant end plates, and means for igniting a test sample in said chamber.

2. The test apparatus claim 1 wherein said body is a cylinder having external on said one end around said access opening and closure means include:

a removable cover plate closing said access opening; sealing means disposed between said cover plate and said one end; and a removable ring having internal threads and an inwardly-directed shoulder to be engaged with said cover plate for releasably clamping said cover plate to said one end when said removable ring is threadedly coupled to said external threads with said cover plate disposed between said one end and said shoulder as well as for urging sealing means into sealing engagement with said one end around said access opening.

3. The test apparatus of claim 2 wherein the outward portion of said lateral opening is enlarged for receiving said window and further including:

reinforcing means for strengthening the wall of said body around said outward portion of said lateral opening to withstand elevated gas pressures in said chamber.

4. The test apparatus of claim 2 wherein said means for igniting a test sample include an electrical igniter for mounting on a test sample to initiate burning thereof in said chamber and further including;

an electrical feedthrough connector in said cover plate; conductor means in said electrical feedthrough connector for connecting said electrical igniter to a power source outside of said test apparatus with said cover plate clamped to said one end to seal said access opening; and a removable receptacle in said chamber for collecting molten materials falling from a burning test sample.

5. The test apparatus of claim 2 wherein said flame-resistant tubular liners and end plates are respectively formed of a metal selected from the group consisting of copper nickel and essentially non-flammable monel alloys.

6. The test apparatus of claim 1 further including:

a removable receptacle in said chamber for collecting molten materials falling from a test sample as it is burning in said chamber.

7. The test apparatus of claim 6 wherein said means for igniting a test sample include an electrical igniter for mounting on a test sample to be burned in said chamber.

8. The test apparatus of claim 7 further including:

means for connecting an electrical power source outside of said test apparatus to said electrical igniter inside of said chamber.

9. The test apparatus of claim 2 wherein said body is in an upright position with said cover plate clamped to the lower and of said body and said means for supporting a test sample include:

an upright removably mounted on said cover plate; and an outstanding bracket on said upright for dependently suspending a test sample in said chamber.

10. The test apparatus of claim 9 wherein said means for igniting a test sample include an electrical igniter for mounting on a test sample to be burned in said chamber.

11. The test apparatus of claim 10 further including:

a removable receptacle disposed in said chamber below said bracket for collecting molten materials falling from a test sample burning in said chamber.

12. Test apparatus for evaluating samples of materials in a controlled environment comprising:

a thick-walled tubular body with an open-ended axial bore and having inlet and outlet gas ports in the wall of said tubular body in communication with its said axial bore; first and second end-closure means respectively installed on each end of said tubular body for fluidly sealing the open ends of said axial bore and individually removable for providing unrestricted access into said tubular body from each end of its said axial bore;

viewing means for observing selected portions of said axial bore including a plurality of lateral openings at selected locations in said wall, a transparent window removably disposed in each of said lateral openings, and fluid-sealing means removably disposed in each of said lateral openings for sealing said windows therein: and means for defining a high-temperature test chamber for enclosing a combustible test sample in said tubular body including a heat-resistant sleeve having side openings and removably disposed in said axial bore with its said side openings respectively aligned with said lateral openings, a flame-resistant tubular liner having side openings and removably disposed within said sleeve with its said side openings respectively aligned with said lateral openings, a transparent barrier removably disposed in each of said lateral openings between said windows and said sleeve, a flame-resistant liner tube removably disposed in each of said lateral openings between said transparent barriers and said tubular liner, first and second flame-resistant end plates removably disposed at the opposite ends of said heat-resistant sleeve for protecting said first and second enclosure means respectively, and means for igniting a test sample in said test chamber.

13. The test apparatus of claim 12 wherein two of said lateral openings are on opposite sides of said tubular body for monitoring one interval of said test chamber and other of said lateral openings are disposed at other locations on said tubular body for monitoring other intervals of said test chamber.

14. The test apparatus of claim 12 wherein said flame-resistant liners and end plates are formed of a metal selected from the group consisting of copper, nickel and essentially non-flammable monel alloys; and said heat-resistant sleeve is formed of a heat-resistant ceramic.

15. The test apparatus of claim 12 further including: means for supporting a test sample at a selected location in said test chamber: and
 a removable receptacle in said test chamber for collecting molten materials falling from a test sample burning in said test chamber.

16. The test apparatus of claim 15 wherein said means for igniting a test sample include an electrical igniter for mounting on a test sample to be supported at said selected location.

17. The test apparatus of claim 15 wherein said lateral openings include a group of first openings located on opposite sides of one portion of said tubular body for passing X-ray energy through a test sample burning in said test chamber and a group of second openings located in other portions of said tubular body for observing other intervals of said test chamber.

18. The test apparatus of claim 17 further including: heat-responsive instrumentation means within each of said second openings outside of their respective windows for providing measurements representative of the temperatures at said other intervals of said test chamber.

19. The test apparatus of claim 12 wherein said lateral openings are spaced around a circumferential wall portion of said tubular body and each of said lateral openings respectively defines an enlarged-diameter outward end portion for receiving one of said windows and one of said transparent barriers as well as for providing an outwardly-facing annular shoulder supporting the inwardly-facing edges of said transparent barrier and further including:
 a plurality of annular flanges having reduced-diameter openings respectively aligned with said outward end portions of said lateral openings to provide inwardly-facing annular shoulders for supporting the outwardly-facing edges of said windows; and
 means removably securing said annular flanges on said circumferential wall portion of said tubular body to retain said windows and said transparent barriers in said outward end portions of said lateral openings.

20. The test apparatus of claim 19 further including: reinforcing means for strengthening said circumferential wall portion of said tubular body around each of said lateral openings to withstand elevated gas pressures in said chamber.

21. The test apparatus of claim 20 wherein said flame-resistant liners and end plates are formed of a metal selected from the group consisting of copper, nickel and essentially non-flammable monel alloys; and said heat-resistant sleeve is formed of a heat-resistant ceramic.

22. Test apparatus for evaluating samples of materials in a controlled environment comprising:
 an upright thick-walled tubular body having a reinforced intermediate portion and open upper and lower body ends with external threads therearound;
 inlet and outlet gas ports in said tubular body providing communication with an axial bore of said tubular body; upper and lower end-closure means mounted on said upper and lower body ends for fluidly sealing said axial bore and separately removable for providing access into said axial bore from each of said open body ends, each of said upper and lower end-closure means including a removable cover plate, a fluid seal disposed between said cover plate and said body end, and a removable ring having an inwardly-directed shoulder for engaging said fluid seal with said body end and internal threads to releasably clamp said cover plate over said body end whenever said removable ring is threadedly coupled to said external threads with said cover plate disposed between said body end and said shoulder on said removable ring;
 viewing means for observing a selected portion of said axial bore including a plurality of lateral openings spaced around said reinforced intermediate portion of said tubular body and counterbored at their outer ends for providing enlarged bore portions defining outwardly-facing annular shoulders, a transparent thermal barrier removably disposed in each of said enlarged bore portions on said outwardly-facing shoulder, a transparent window removably disposed in each of said enlarged bore portions over said transparent barriers, sealing means removably disposed in each of said enlarged bore portions for fluidly sealing said windows therein, a flange having a reduced-diameter opening removably disposed over each of said enlarged bore portions providing inwardly-facing shoulders for supporting the outwardly-facing marginal surfaces of said windows, and means removably securing said flanges on said tubular body for retaining said windows, transparent barriers and sealing means in said enlarged bore portions; and
 means for defining a high-temperature test chamber for enclosing a combustible test sample in said tubular body including a heat-resistant insulating sleeve having side openings and removably disposed in said axial bore with each of its said side openings respectively aligned with one of said lateral openings, an expendable flame-resistant tubular liner having side openings and removably disposed in said heat-resistant insulating sleeve with each of said side openings respectively aligned with one of said lateral openings, an expendable flame-resistant liner tube removably disposed in each of said lateral openings between said transparent thermal barrier and said flame-resistant tubular liner, upper and lower expendable flame-resistant end plates removably disposed in said tubular body at the opposite ends of said heat-resistant insulating sleeve for protecting the inward surfaces of said upper and lower cover plates, and means for selectively igniting a test sample in said test chamber.

23. The test apparatus of claim 22 wherein said flame-resistant liners and said flame-resistant end plates are respectively formed of a metal selected from the group consisting of copper, nickel and essentially non-flammable monel alloys; and said heat-resistant insulating sleeve is formed of a heat-resistant ceramic.

24. The test apparatus of claim 22 further including:
a plurality of second lateral openings in said tubular body;
a plurality of second side openings in said expendable flame-resistant tubular liner and in said heat-resistant insulating sleeve and aligned with said second lateral openings;
a second transparent thermal barrier removably disposed in each of said second lateral openings;
a second transparent window removably disposed in each of said second lateral openings over said second transparent barriers;
second sealing means removably disposed in each of said second lateral openings for fluidly sealing said second windows therein;
an expendable flame-resistant liner tube removably disposed in each of said second lateral openings between said flame-resistant tubular liner and said second transparent barriers; and
heat-responsive instrumentation means within said second openings outside of said second windows for providing a plurality of output measurements representative of the temperatures in other intervals of said test chamber.

25. The test apparatus of claim 24 wherein said flame-resistant liners and said flame-resistant end plates are respectively formed of a metal selected from the group consisting of copper, nickel and essentially non-flammable monel alloys; and said heat-resistant insulating sleeve is formed of a heat-resistant ceramic.

26. The test apparatus of claim 22 further including:
a receptacle removably dispersed in said test chamber for collecting molten materials falling from a test sample as it is burning within said test chamber.

27. The test apparatus of claim 26 further including:
an upright removably mounted on said lower cover plate; and
an outstanding bracket removably mounted on said upright for dependently suspending a test sample in said test chamber above said receptacle.

28. The test apparatus of claim 26 wherein said means for selectively igniting a test sample inside of said test chamber include an electrical igniter for mounting on a test sample to be burned in said test chamber.

29. The test apparatus of claim 28 further including:
a feedthrough connector in said lower cover plate:
conductor means in said feedthrough connector connecting said electrical igniter to an external power source outside of said test chamber when said lower cover plate is clamped to said lower body end.

30. The test apparatus of claim 26 further including:
a tubular upright removably mounted on said lower cover plate and having an internal bore defining an interior passage for carrying instrumentation wiring;
an outstanding bracket removably mounted on said upright for dependently suspending a test sample in said test chamber above said receptacle; and
passage means in said lower cover plate providing a fluid seal around instrumentation wiring extending through said internal bore of said tubular upright to instrumentation outside of said test apparatus.

31. The test apparatus of claim 30 wherein said means for selectively igniting a test sample inside of said test chamber include an electrical igniter for mounting on a test sample to be suspended from said outstanding bracket in said test chamber.

32. The test apparatus of claim 31 further including:
a feedthrough connector in said lower cover plate; and
conductor means in said feedthrough connector connecting said electrical igniter to a power source outside of said test chamber when said lower cover plate is clamped to said lower body end.

* * * * *